(12) United States Patent
Abe

(10) Patent No.: US 8,546,599 B2
(45) Date of Patent: Oct. 1, 2013

(54) TERT-BUTYLPHENYL SULFONATE COMPOUND, NONAQUEOUS ELECTROLYTE SOLUTION FOR LITHIUM SECONDARY BATTERY USING THE SAME, AND LITHIUM SECONDARY BATTERY USING THE SAME

(75) Inventor: Koji Abe, Yamaguchi-ken (JP)

(73) Assignee: Ube Industries, Ltd., Yamaguchi-Ken (JP)

( * ) Notice: Subject to any disclaimer, the term of this patent is extended or adjusted under 35 U.S.C. 154(b) by 798 days.

(21) Appl. No.: 12/530,206

(22) PCT Filed: Mar. 6, 2008

(86) PCT No.: PCT/JP2008/000462
§ 371 (c)(1),
(2), (4) Date: Nov. 9, 2009

(87) PCT Pub. No.: WO2008/123014
PCT Pub. Date: Oct. 16, 2008

(65) Prior Publication Data
US 2010/0055576 A1    Mar. 4, 2010

(30) Foreign Application Priority Data

Mar. 6, 2007 (JP) ................................. 2007-055014
Sep. 6, 2007 (JP) ................................. 2007-231893
Oct. 1, 2007 (JP) ................................. 2007-257690

(51) Int. Cl.
*C07C 309/65*    (2006.01)
*C07C 309/72*    (2006.01)
*H01M 6/16*    (2006.01)

(52) U.S. Cl.
USPC ................................ 558/56; 558/44; 429/337

(58) Field of Classification Search
USPC ..................................... 429/337; 558/56, 44
See application file for complete search history.

(56) References Cited

U.S. PATENT DOCUMENTS 6,670,078 B1    12/2003 Sato et al.
8,283,508 B2 *  10/2012 Abe et al. ...................... 585/469

FOREIGN PATENT DOCUMENTS

| EP | 1 030 399 A1 | 8/2000 |
| JP | 63-104903 A | 5/1988 |
| JP | 03-047791 A | 2/1991 |
| JP | 04-160766 A | 6/1992 |
| WO | WO9916144 A1 | 4/1999 |

OTHER PUBLICATIONS

Himeshima et al. (J. Am. Chem. Soc. 1985, 107. 5286-5288).*
International Search Report for PCT/JP2008/000462 dated on Apr. 1, 2008.

* cited by examiner

*Primary Examiner* — Jason M Nolan
(74) *Attorney, Agent, or Firm* — Kenealy Vaidya LLP

(57) ABSTRACT

The disclosed subject matter relate to a di-tert-butylphenyl alkylsulfonate compound, tert-butylphenyl alkylsulfonate compound, di-tert-butylphenyl arylsulfonate compound or tert-butylphenyl arylsulfonate compound useful as an intermediate raw material of a pharmaceutical, agricultural chemical, electronic material or polymer material and the like, or as a battery material, and also provides a nonaqueous electrolytic solution for a lithium secondary battery having superior cycle performance and other battery properties through the use thereof, and a lithium secondary battery. The disclosed embodiments further relate to a nonaqueous electrolytic solution for use as in a lithium secondary battery containing, in a nonaqueous electrolytic solution in which an electrolyte salt is dissolved in a nonaqueous solvent, 0.01 to 10% by weight of a di-tert-butylphenyl alkylsulfonate compound, tert-butylphenyl alkylsulfonate compound, di-tert-butylphenyl arylsulfonate compound or tert-butylphenyl arylsulfonate compound, and to a lithium secondary battery and a compound.

22 Claims, No Drawings

TERT-BUTYLPHENYL SULFONATE COMPOUND, NONAQUEOUS ELECTROLYTE SOLUTION FOR LITHIUM SECONDARY BATTERY USING THE SAME, AND LITHIUM SECONDARY BATTERY USING THE SAME

CROSS REFERENCE TO RELATED APPLICATION

This application is a U.S. national phase filing under 35 U.S.C. §371 of PCT Application No. PCT/JP2008/000462, filed Mar. 6, 2008, and claims priority under 35 U.S.C. §119 to Japanese patent application no. 2007-055014, filed Mar. 6, 2007, Japanese patent application no. 2007-231893, filed Sep. 6, 2007, and Japanese patent application no. 2007-257690, filed Oct. 1, 2007, the entireties of which are all incorporated by reference herein.

BACKGROUND

1. Field

The disclosed embodiments relate to a di-tert-butylphenyl alkylsulfonate compound, tert-butylphenyl alkylsulfonate compound, di-tert-butylphenyl arylsulfonate compound and tert-butylphenyl arylsulfonate compound useful as an intermediate material of a pharmaceutical, agricultural chemical, electronic material or polymer material and the like, or as a battery material, to an nonaqueous electrolytic solution for a lithium secondary battery having superior cycle performance and other battery properties through the use of a nonaqueous electrolytic solution for a lithium secondary battery that uses the above-mentioned compounds, and to a lithium secondary battery using the above-mentioned compounds.

2. Related Art

In recent years, lithium secondary batteries have come to be widely used as power supplies for driving compact electronic devices and the like. Lithium secondary batteries are mainly composed of a positive electrode and negative electrode containing materials capable of occluding and releasing lithium, and a nonaqueous electrolytic solution containing a lithium salt. Examples of these nonaqueous electrolytic solutions include carbonates such as ethylene carbonate (EC) or propylene carbonate (PC).

Known examples of materials used for the negative electrode of lithium secondary batteries include lithium metal, metal compounds capable of occluding and releasing lithium (such as simple metals, oxides or alloys of lithium), and carbon materials. Among carbon materials in particular, non-aqueous electrolyte secondary batteries are widely used and employ a carbon material capable of occluding and releasing lithium such as coke or graphite (artificial graphite, natural graphite). In lithium secondary batteries using highly crystallized carbon materials, such as natural graphite or artificial graphite in particular, EC or PC and the like used for the nonaqueous electrolyte solvent are known to cause a decrease in battery performance due to the occurrence of partial electrochemical reductive decomposition on the negative electrode surface during the course of repeated charging and discharging.

Moreover, studies have been conducted on negative electrodes using materials other than lithium metal or carbon materials, such as tin or silicon for the negative electrode material. However, since tin alloys or silicon alloys that have occluded lithium are highly active, carbonic acid esters present in the electrolytic solution end up being decomposed, while also resulting in the problem of deactivation of the occluded lithium.

On the other hand, since lithium secondary batteries using materials such as $LiCoO_2$, $LiMn_2O_4$, $LiNiO_2$ or $LiFePO_4$ for the positive electrode exhibit a high voltage of 3.5 V or more accompanying insertion and extraction of lithium ions based on lithium as a reference, batteries having a high energy density are able to be obtained. Conversely, due to the high voltage, decomposition products cause a decrease in battery performance due to the local occurrence of partial oxidative decomposition in the case the solvent in the nonaqueous electrolytic solution has reached a high temperature during charging. This is thought to be caused by an electrochemical oxidative decomposition reaction at the interface between the positive electrode material and nonaqueous electrolytic solution.

As previously stated, when an electrolytic solution decomposes on the positive electrode or negative electrode, gas is generated and the battery swells or electrolytic solution decomposition products become adhered to the electrodes, thereby causing a decrease in cycle performance and other aspects of battery performance.

Under such circumstances, in electronic devices in which lithium secondary batteries are installed, power consumption increases and capacity continues to rise, resulting in an environment in which decomposition of the electrolytic solution occurs even more easily, thereby resulting in the problem of further exacerbation of cycle performance and other battery properties.

Although Japanese Patent Application Laid-open No. H04-160766 discloses a lithium secondary battery in which benzene triflate (phenyl trifluoro methanesulfonate) and xylene triflate are dissolved in a nonaqueous electrolytic solution, satisfactory cycle performance is still unable to be obtained despite using these compounds.

SUMMARY

One of the aspects of the disclosed embodiments is to provide a di-tert-butylphenyl alkylsulfonate compound, tert-butylphenyl alkylsulfonate compound, di-tert-butylphenyl arylsulfonate compound and tert-butylphenyl arylsulfonate compound useful as an intermediate material or a pharmaceutical, agricultural chemical, electronic material or polymer material and the like, or as a battery material, a nonaqueous electrolytic solution for a lithium secondary battery using the same that has superior cycle performance and other battery properties, and a lithium secondary battery using the same.

As a result of extensive studies it has been found that, in a nonaqueous electrolytic solution in which an electrolyte salt is dissolved in a nonaqueous solvent, superior cycle performance can be obtained by synthesizing a di-tert-butylphenyl alkylsulfonate compound, tert-butylphenyl alkylsulfonate compound, di-tert-butylphenyl arylsulfonate compound or tert-butylphenyl arylsulfonate compound having one or two tert-butyl groups in a benzene ring of the phenyl group of a phenyl alkylsulfonate or phenyl arylsulfonate, and then adding this to the nonaqueous electrolytic solution, thereby leading to completion of the disclosed embodiments.

Namely, the disclosed embodiments include a tert-butylphenyl alkylsulfonate compound or tert-butylphenyl arylsulfonate compound represented by general formula (I):

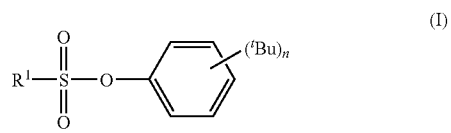

wherein, $R^1$ represents a substituted or non-substituted alkyl group or substituted or non-substituted phenyl group, and n represents an integer of 1 to 2, provided that in the case n=1, the substitution position of the $^tBu$ group is the 2 position or 3 position, in the case the substitution position of the $^tBu$ group is the 2 position, $R^1$ represents a non-substituted alkyl group having 2 to 4 carbon atoms, in the case the substitution position of the $^tBu$ group is the 3 position, $R^1$ represents a non-substituted alkyl group having 1 to 4 carbon atoms, and in the case n=2, the substitution positions of the $^tBu$ group are any of the 2,4 position, 2,5 position, 2,6 position or 3,5 position, and in the case $^tBu$ groups are present at the 3,5 position, $R^1$ represents a non-substituted alkyl group having 1 to 4 carbon atoms or a non-substituted phenyl group.

A compound of the above-mentioned general formula (I) includes compounds selected from 2,4-di-tert-butylphenyl methanesulfonate, 2,6-di-tert-butylphenyl methanesulfonate, 3,5-di-tert-butylphenyl methanesulfonate, 2,5-di-tert-butylphenyl methanesulfonate, 2,4-di-tert-butylphenyl ethanesulfonate, 2,6-di-tert-butylphenyl ethanesulfonate, 3,5-di-tert-butylphenyl ethanesulfonate and 2,4-di-tert-butylphenyl trifluoromethanesulfonate.

In addition, a compound represented by the above-mentioned general formula (I) includes compounds selected from 2,4-di-tert-butylphenyl benzenesulfonate or 2,4-di-tert-butylphenyl p-toluenesulfonate.

A compound represented by the above-mentioned general formula (I) includes tert-butylphenyl alkylsulfonate compounds selected from 3-tert-butylphenyl methanesulfonate, 2-tert-butylphenyl ethanesulfonate and 3-tert-butylphenyl ethanesulfonate.

The nonaqueous electrolytic solution of the disclosed embodiments in which an electrolyte salt is dissolved in a nonaqueous solvent is a nonaqueous electrolytic solution for a lithium secondary battery containing 0.01 to 10% by weight of a tert-butylphenyl alkylsulfonate compound or a tert-butylphenyl arylsulfonate compound represented by general formula (II) based on the weight of the nonaqueous electrolytic solution.

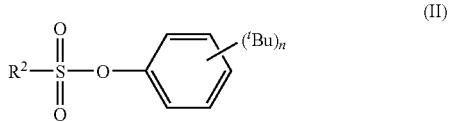

wherein, $R^2$ represents a substituted or non-substituted alkyl group or substituted or non-substituted aryl group, and n represents an integer of 1 to 2, provided that in the case n=2, the substitution positions of the $^tBu$ group are any of the 2,4 position, 2,5 position, 2,6 position or 3,5 position.

In addition, a lithium secondary battery having a positive electrode, a negative electrode and a nonaqueous electrolytic solution in which an electrolyte salt is dissolved in a nonaqueous solvent is a lithium secondary battery containing 0.01 to 10% by weight of a tert-butylphenyl alkylsulfonate compound or a tert-butylphenyl arylsulfonate compound represented by general formula (II) based on the weight of the nonaqueous electrolytic solution.

In addition, a lithium secondary battery using a nonaqueous electrolytic solution thereof a tert-butylphenyl alkylsulfonate compound or tert-butylphenyl arylsulfonate compound of the disclosed embodiments has superior cycle performance and storage properties.

DETAILED DESCRIPTION OF EXEMPLARY EMBODIMENTS

The following provides a detailed description of a di-tert-butylphenyl alkylsulfonate compound or di-tert-butylphenyl arylsulfonate compound and tert-butylphenyl alkylsulfonate compound or tert-butylphenyl arylsulfonate compound of the disclosed embodiments, a nonaqueous electrolytic solution for a lithium secondary battery using the same, and a lithium secondary battery using the same.

The di-tert-butylphenyl alkylsulfonate compound, di-tert-butylphenyl arylsulfonate compound, tert-butylphenyl alkylsulfonate compound and tert-butylphenyl arylsulfonate compound of the disclosed embodiments are represented by the following general formula (I):

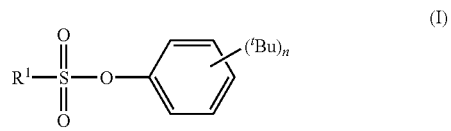

wherein, $R^1$ represents a substituted or non-substituted alkyl group or substituted or non-substituted phenyl group, and n represents an integer of 1 to 2, provided that in the case n=1, the substitution position of the $^tBu$ group is position 2 or position 3, in the case the substitution position of the $^tBu$ group is position 2, $R^1$ represents a non-substituted alkyl group having 2 to 4 carbon atoms, in the case the substitution position of the $^tBu$ group is position 3, $R^1$ represents a non-substituted alkyl group having 1 to 4 carbon atoms, and in the case n=2, the substitution positions of the $^tBu$ group are any of the 2,4 position, 2,5 position, 2,6 position or 3,5 position, and in the case $^tBu$ groups are present at the 3,5 position, R represents a non-substituted alkyl group having 1 to 4 carbon atoms or a non-substituted phenyl group.

An "alkyl group substituent" includes, for example, fluorine, and a "phenyl group substituent" includes, for example, a short chain alkyl group.

The di-tert-butylphenyl alkylsulfonate compound, di-tert-butylphenyl arylsulfonate compound, tert-butylphenyl alkylsulfonate compound and tert-butylphenyl arylsulfonate compound represented by general formula (I) of the disclosed embodiments are novel compounds. Specific examples of these compounds include 2,4-di-tert-butylphenyl methanesulfonate, 2,6-di-tert-butylphenyl methanesulfonate, 3,5-di-tert-butylphenyl methanesulfonate, 2,5-di-tert-butylphenyl methanesulfonate, 2,4-di-tert-butylphenyl ethanesulfonate, 2,6-di-tert-butylphenyl ethanesulfonate, 3,5-di-tert-butylphenyl ethanesulfonate, 2,4-di-tert-butylphenyl trifluoromethanesulfonate, 2,4-di-tert-butylphenyl benzenesulfonate, 2,4-di-tert-butylphenyl p-toluenesulfonate, 3-tert-butylphenyl methanesulfonate, 2-tert-butylphenyl ethanesulfonate, and 3-tert-butylphenyl ethanesulfonate.

The tert-butylphenyl alkylsulfonate compound or tert-butylphenyl arylsulfonate compound used in the nonaqueous electrolytic solution for a lithium secondary battery of the disclosed embodiments and in a lithium secondary battery using the same is represented by the following general formula (II):

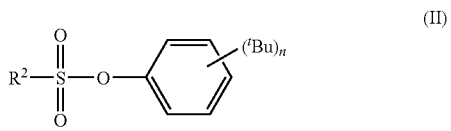

wherein, $R^2$ represents a substituted or non-substituted alkyl group or substituted or non-substituted aryl group, and n represents an integer of 1 to 2, provided that in the case n=2, the substitution positions of the $^tBu$ group are any of the 2,4 position, 2,5 position, 2,6 position or 3,5 position.

Di-tert-butylphenyl Alkylsulfonate Compound or Di-tert-butylphenyl Arylsulfonate Compound The di-tert-butylphenyl compounds of the disclosed embodiments are represented by the following general formula (III), $R^2SO_2$ is $R^3$ and n=2 in the above-mentioned general formula (II):

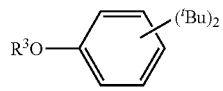

(III)

wherein, $R^3$ represents an alkanesulfonyl group or arylsulfonyl group, and the $^tBu$ group represents a tert-butyl group, provided that the substitution positions of the $^tBu$ group are any of the 2,4 position, 2,5 position, 2,6 position or 3,5 position.

An alkanesulfonyl group of the compounds of the disclosed embodiments is a substituted or non-substituted alkanesulfonyl group. In addition, an arylsulfonyl group of the compounds of the disclosed embodiments is a substituted or non-substituted arylsulfonyl group.

Although there are no particular limitations on the di-tert-butylphenyl alkylsulfonate compound or di-tert-butylphenyl arylsulfonate compound, the alkyl group of the di-tert-butylphenyl alkylsulfonate compound or di-tert-butylphenyl arylsulfonate compound is an alkyl group having 1 to 6 carbon atoms, while the aryl group is an aryl group having 6 to 12 carbon atoms. Specific examples include 2,4-di-tert-butylphenyl methanesulfonate, 2,6-di-tert-butylphenyl methanesulfonate, 3,5-di-tert-butylphenyl methanesulfonate, 2,5-di-tert-butylphenyl methanesulfonate, 2,4-di-tert-butylphenyl ethanesulfonate, 2,6-di-tert-butylphenyl ethanesulfonate, 3,5-di-tert-butylphenyl ethanesulfonate, 2,5-di-tert-butylphenyl ethanesulfonate, 2,4-di-tert-butylphenyl trifluoromethanesulfonate, 2,6-di-tert-butylphenyl trifluoromethanesulfonate, 3,5-di-tert-butylphenyl trifluoromethanesulfonate, 2,5-di-tert-butylphenyl trifluoromethanesulfonate, 2,4-di-tert-butylphenyl benzenesulfonate, 2,6-di-tert-butylphenyl benzenesulfonate, 3,5-di-tert-butylphenyl benzenesulfonate, 2,5-di-tert-butylphenyl benzenesulfonate, 2,4-di-tert-butylphenyl p-toluenesulfonate, 2,6-di-tert-butylphenyl p-toluenesulfonate, 3,5-di-tert-butylphenyl p-toluenesulfonate, and 2,5-di-tert-butylphenyl p-toluenesulfonate.

The alkyl group or aryl group of the di-tert-butylphenyl alkylsulfonate compound or di-tert-butylphenyl arylsulfonate compound is preferably a methyl group, ethyl group, phenyl group or p-tolyl group, particularly preferably a methyl group or ethyl group, and most preferably a methyl group.

Among the combinations of substitution positions of the two tert-butyl groups of the di-tert-butylphenyl alkylsulfonate compound or di-tert-butylphenyl arylsulfonate compound, the 2,4 position, 2,6 position or 3,5 position is particularly preferable, and the 2,4 position or 2,6 position is most preferable.

In particular, 2,4-di-tert-butylphenyl methanesulfonate, 2,4-di-tert-butylphenyl ethanesulfonate, 2,4-di-tert-butylphenyl benzenesulfonate and 2,4-di-tert-butylphenyl p-toluenesulfonate are preferable, 2,4-di-tert-butylphenyl methanesulfonate and 2,4-di-tert-butylphenyl ethanesulfonate are particularly preferable, and 2,4-di-tert-butylphenyl methanesulfonate is most preferable.

Tert-butylphenyl Alkylsulfonate Compound or Tert-butylphenyl Arylsulfonate Compound The tert-butylphenyl compounds of the disclosed embodiments are represented by the following general formula (IV) when n=1 in the above-mentioned general formula (II):

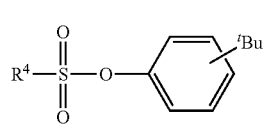

(IV)

wherein, $R^4$ represents an alkyl group or aryl group, and the $^tBu$ group represents a tert-butyl group, provided that the substitution position of the $^tBu$ group is the 2 position, 3 position or 4 position.

The alkyl group of the compounds of the disclosed embodiments is a substituted or non-substituted alkyl group. In addition, the aryl group of the compounds of the disclosed embodiments is a substituted or non-substituted aryl group.

Although there are no particular limitations on the tert-butylphenyl alkylsulfonate compound or tert-butylphenyl arylsulfonate compound, the alkyl group of the tert-butylphenyl alkylsulfonate compound or tert-butylphenyl arylsulfonate compound is an alkyl group having 1 to 6 carbon atoms and preferably an alkyl group having 2 to 4 carbon atoms, while the aryl group is an aryl group having 6 to 12 carbon atoms and preferably an aryl group having 6 to 10 carbon atoms.

More specifically, 2-tert-butylphenyl methanesulfonate, 3-tert-butylphenyl methanesulfonate, 4-tert-butylphenyl methanesulfonate, 2-tert-butylphenyl ethanesulfonate, 3-tert-butylphenyl ethanesulfonate, 4-tert-butylphenyl ethanesulfonate, 2-tert-butylphenyl trifluoromethanesulfonate, 3-tert-butylphenyl trifluoromethanesulfonate, 4-tert-butylphenyl trifluoromethanesulfonate, 2-tert-butylphenyl benzenesulfonate, 3-tert-butylphenyl benzenesulfonate, 4-tert-butylphenyl benzenesulfonate, 2-tert-butylphenyl p-toluenesulfonate, 3-tert-butylphenyl p-toluenesulfonate and 4-tert-butylphenyl p-toluenesulfonate are preferable due to their satisfactory cycle performance and storage properties.

The alkyl group or aryl group of the tert-butylphenyl alkylsulfonate compound or tert-butylphenyl arylsulfonate compound is preferably a methyl group, ethyl group, phenyl group or p-tolyl group, particularly preferably a methyl group or ethyl group, and most preferably a methyl group.

The substitution position of the tert-butyl group of the tert-butylphenyl alkylsulfonate compound or tert-butylphenyl arylsulfonate compound is preferably the 2 position or 4 position and particularly preferably the 2 position.

Nonaqueous Electrolytic Solution

The nonaqueous electrolytic solution of the disclosed embodiments is a nonaqueous electrolytic solution in which an electrolyte salt is dissolved in a nonaqueous solvent to which is added 0.01 to 10% by weight of one type or two or more types of a di-tert-butylphenyl alkylsulfonate compound, tert-butylphenyl alkylsulfonate compound, di-tert-butylphenyl arylsulfonate compound or tert-butylphenyl arylsulfonate compound based on the weight of the nonaqueous electrolytic solution.

In the nonaqueous electrolytic solution of the disclosed embodiments, if the content of the one type or two or more types of the di-tert-butylphenyl alkylsulfonate compound, tert-butylphenyl alkylsulfonate compound, di-tert-butylphenyl arylsulfonate compound or tert-butylphenyl arylsulfonate compound contained in the nonaqueous electrolytic solution exceeds 10% by weight, cycle performance may decrease or adequate effects may not be obtained for inhibiting generation of gas during storage, while if the above-mentioned content is less than 0.01% by weight, adequate effects for cycle performance and inhibiting generation of gas may not be obtained. Thus, the content of the di-tert-butylphenyl alkylsulfonate compound, tert-butylphenyl alkylsulfonate compound, di-tert-butylphenyl arylsulfonate compound or tert-butylphenyl arylsulfonate compound is preferably 0.01% by weight or more, more preferably 0.1% by weight or more and most preferably 1% by weight based on the weight of the nonaqueous electrolytic solution. In addition, the upper limit thereof is preferably 10% by weight or less, more preferably 7% by weight or less and most preferably 5% by weight or less.

If the one type or two or more types of di-tert-butylphenyl alkylsulfonate compound, tert-butylphenyl alkylsulfonate compound, di-tert-butylphenyl arylsulfonate compound or tert-butylphenyl arylsulfonate compound in the nonaqueous electrolytic solution is added within the range of 0.01% by weight to 10% by weight, a surface film of suitable thickness is formed on the negative electrode, and electrochemical reductive decomposition by the solvent in the nonaqueous electrolytic solution is inhibited. On the other hand, a surface film is also formed on the positive electrode, and this is presumed to inhibit electrochemical oxidative decomposition by the solvent in the nonaqueous electrolytic solution.

Nonaqueous Solvent

Examples of nonaqueous solvents used for the nonaqueous solvent used in the nonaqueous electrolytic solution of the disclosed embodiments include cyclic carbonates, linear carbonates, linear esters, ethers, amides, phosphoric acid esters, sulfones, lactones and nitriles.

Examples of cyclic carbonates include ethylene carbonate (EC), propylene carbonate (PC), butylene carbonate (BC), fluoroethylene carbonate (FEC), vinylene carbonate (VC) and vinylethylene carbonate (VEC). The use of at least one type of EC or PC having a high dielectric constant for the cyclic carbonate in particular is preferable since the electrical conductivity of the electrolytic solution can be improved, while combining with the use of at least one type of VC, VEC or FEC is more preferable since cycle performance is improved. Although only one type of these solvents may be used, combining two to four types is preferable since cycle performance is improved. Examples of preferable combinations of these cyclic carbonates include EC and VC, PC and VC, FEC and VC, EC, PC and VC, EC, FEC and VC, FEC, PC and VC and FEC, EC, PC and VC. The content of cyclic carbonate used is preferably within the range of 10 to 40% by volume based on the total volume of the nonaqueous solvent. If the content is less than 10% by volume, electrical conductivity of the electrolytic solution decreases and cycle performance tends to decrease, while if the content exceeds 40% by volume, the viscosity of the electrolytic solution increases and cycle performance tends to decrease. Thus, the content is preferably within the above-mentioned range.

Examples of linear carbonates include asymmetrical linear carbonates such as methyl ethyl carbonate (MEC), methyl propyl carbonate, methyl isopropyl carbonate, methyl butyl carbonate or ethyl propyl carbonate, and symmetrical linear carbonates such as dimethyl carbonate (DMC), diethyl carbonate (DEC), dipropyl carbonate or dibutyl carbonate, and the inclusion of an asymmetrical linear carbonate is particularly preferable since cycle performance is improved.

One type of these solvents may be used, and in the case two or more types are used in combination, cycle performance is improved, thereby making this preferable.

The content of linear carbonate used is preferably 60 to 90% by volume based on the total volume of the nonaqueous electrolytic solution. If the content is less than 60% by volume, electrolytic solution viscosity increases and cycle performance tends to decrease. In addition, if the content exceeds 90% by volume, electrical conductivity of the electrolytic solution decreases and cycle performance tends to decrease. Thus, the content is preferably within the above-mentioned range.

Examples of linear esters include methyl propionate, methyl pivalate, butyl pivalate, hexyl pivalate, octyl pivalate, dimethyl oxalate, ethyl methyl oxalate and diethyl oxalate, while examples of ethers include tetrahydrofuran, 2-methyl tetrahydrofuran, 1,3-dioxane, 1,4-dioxane, 1,2-dimethoxyethane, 1,2-diethoxyethane and 1,2-dibutoxyethane. Examples of amides include dimethylformamide, examples of phosphoric acid esters include trimethyl phosphate, tributyl phosphate and trioctyl phosphate, examples of sulfones include sulfolane, examples of lactones include γ-butyrolactone, γ-valerolactone and α-angelica lactone, examples of nitriles include acetonitrile, succinonitrile and adiponitrile, and examples of compounds having an S=O bond include 1,3-propane sultone (PS), ethylene sulfite, 1,4-butanediol dimethanesulfonate, 1,3-butanediol dimethanesulfonate and divinyl sulfone, and these can be suitably used in combination.

The above-mentioned nonaqueous solvent is usually used as a mixture. Examples of combinations thereof include cyclic carbonates and linear carbonates, cyclic carbonates, linear carbonates and lactones, cyclic carbonates, linear carbonates and ethers, and cyclic carbonates, linear carbonates and linear esters.

Among these combinations, combinations of cyclic carbonates and linear carbonates are preferable, and more specifically, combinations of cyclic carbonates such as EC or PC and linear carbonates such as DMC, MEC or DEC are particularly preferable since cycle performance can be improved.

The proportion of cyclic carbonate and linear carbonate is such that the ratio of cyclic carbonate to linear carbonate (volume ratio) is preferably 10:90 to 40:60, more preferably 15:85 to 35:65 and particularly preferably 20:80 to 30:70. Cycle performance can be improved as a result of using in the above-mentioned proportions.

Electrolyte Salt

Examples of electrolyte salts used in the disclosed embodiments include lithium salts such as $LiPF_6$, $LiBF_4$ or $LiClO_4$, lithium salts containing linear alkyl groups such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$ or $LiPF_5(is\ O-C_3F_7)$, and lithium salts containing a cyclic alkylene chain such as $(CF_2)_2(SO_2)_2NLi$ or $(CF_2)_3(SO_2)_2NLi$. Among these, particularly preferable electrolyte salts are $LiPF_6$, $LiBF_4$, $LiN(SO_2CF_3)_2$ and $LiN(SO_2C_2F_5)_2$. One type of these electrolyte salts can be used or two or more types can be used in combination.

Examples of preferable combinations of the electrolyte salts include $LiPF_6$ and at least one type selected from the group consisting of $LiBF_4$, $LiN(SO_2CF_3)_2$ and $LiN(SO_2C_2F_5)_2$. Preferable examples include the combination of $LiPF_6$ and $LiBF_4$, the combination of $LiPF_6$ and LiN ($SO_2CF_3)_2$, and the combination of $LiPF_6$ and $LiN(SO_2C_2F_5)_2$. Cycle performance may decrease in the case the ratio (molar ratio) of $LiPF_6$ to $LiBF_4$, $LiN(SO_2CF_3)_2$ or $LiN(SO_2C_2F_5)_2$ is lower than 70:30 or higher than 99:1. Thus, the ratio (molar ratio) of $LiPF_6$ to $LiBF_4$, $LiN(SO_2CF_3)_2$ or $LiN(SO_2C_2F_5)_2$ is preferably within the range of 70:30 to 99:1, and more preferably within the range of 80:20 to 98:2. Cycle performance improves as a result of using in the above-mentioned combinations.

The concentration at which all of these electrolyte salts are used after dissolving is normally preferably 0.3 mol/l (to be represented as M) or more, more preferably 0.5 M or more, and most preferably 0.7 M or more based on the above-mentioned nonaqueous solvent. In addition, the upper limit of that concentration is preferably 2.5 M or less, more preferably 2.0 M or less and most preferably 1.5 M or less.

Other Additives

The nonaqueous electrolytic solution of the disclosed embodiments can ensure battery stability during overcharging by including an aromatic compound. Preferable examples of this aromatic compound include cyclohexylbenzene, fluorocyclohexylbenzene compounds (such as 1-fluoro-2-cyclohexylbenzene, 1-fluoro-3-cyclohexylbenzene or 1-fluoro-4-cyclohexylbenzene), tert-butylbenzene, tert-amylbenzene, 1-fluoro-4-tert-butylbenzene, 1,3-di-tert-butylbenzene, biphenyl, terphenyl (o-, m- and p-forms), diphenyl ether, fluorobenzene, difluorobenzene (o-, m-, and p-forms), 2,4-difluoroanisole and terphenyl partial hydrides (such as 1,2-dicyclohexylbenzene, 2-phenylbicyclohexyl, 1,2-diphenylcyclohexane or o-cyclohexylbiphenyl), and these are preferably added at 0.1 to 10% by weight based on the weight of the nonaqueous electrolytic solution. One type of these compounds may be used or two or more types may be used in combination.

Production of Nonaqueous Electrolytic Solution

The nonaqueous electrolytic solution of the disclosed embodiments can be obtained by, for example, mixing the above-mentioned nonaqueous solvent, and dissolving therein the above-mentioned electrolyte salt and 0.01 to 10% by weight of one type or two or more types of a di-tert-butylphenyl alkylsulfonate compound, tert-butylphenyl alkylsulfonate compound, di-tert-butylphenyl arylsulfonate compound or tert-butylphenyl arylsulfonate compound based on the weight of the nonaqueous electrolytic solution.

At this time, compounds added to the nonaqueous solvent and electrolytic solution used are preferably purified in advance so as to minimize the level of impurities therein within a range that does not significantly lower productivity.

Lithium Secondary Battery

The lithium secondary battery of the disclosed embodiments includes a positive electrode, a negative electrode, and the above-mentioned nonaqueous electrolytic solution in which an electrolyte salt is dissolved in a nonaqueous solvent. Constituent members other than the nonaqueous electrolytic solution, such as the positive electrode and negative electrode, can be used without any particular limitations.

For example, a composite metal oxide with lithium containing cobalt, manganese or nickel can be used as a positive electrode active material. One type of these positive electrode active substances can be used or two or more types can be used in combination.

Examples of such composite metal oxides include $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$ and $LiCu_{0.98}Mg_{0.02}O_2$. In addition, composite metal oxides may also be used in combination in the manner of $LiCoO_2$ and $LiMn_2O_4$, $LiCoO_2$ and $LiNiO_2$ or $LiMn_2O_4$ and $LiNiO_2$.

In addition, a portion of the lithium composite oxide may be substituted with other elements, a portion of the cobalt, manganese or nickel may be substituted with at least one type of element such as Sn, Mg, Fe, Ti, Al, Zr, Cr, V, Ga, Zn, Cu, Bi, Mo or La, a portion of O may be substituted with S or F, or the lithium composite oxide can be coated with a compound containing these elements.

Moreover, a lithium-containing olivine-type phosphate can also be used for the positive electrode active material. Specific examples of such salts include $LiFePO_4$, $LiCoPO_4$, $LiNiPO_4$ and $LiMnPO_4$. In addition, two or more types of these lithium-containing olivine-type phosphates such as $LiFePO_4$, $LiCoPO_4$, $LiNiPO_4$ and $LiMnPO_4$ may be used in combination. In addition, a portion of the iron, cobalt, nickel or manganese comprising a portion of the lithium-containing olivine-type phosphate may be substituted with other elements, and more specifically, may be substituted with at least one other type of element such as Mg, Al, B, Ti, V, Nb, Cu, Zn, Mo, Ca, Sr, W or Zr. Alternatively, the lithium-containing olivine-type phosphate can be coated with a compound containing these elements or a carbon material. Among these lithium-containing olivine-type phosphates, $LiFePO_4$ and $LiCoPO_4$ are preferable.

A lithium-containing olivine-type phosphate can also be used by, for example, mixing with the previously indicated positive electrode active substances.

There are no particular limitations on a conducting agent of the positive electrode provided it is an electron-conducting material that does not cause a chemical change. Examples of such materials include graphite such as natural graphite (such as flake graphite) or artificial graphite, and carbon blacks such as acetylene black, Ketchen black, channel black, furnace black, lamp black or thermal black. In addition, graphite and carbon black may be used by suitably mixing. The amount of conducting agent added to the positive electrode mix substance is preferably 1 to 10% by weight and particularly preferably 2 to 5% by weight.

The positive electrode can be fabricated by mixing the above-mentioned positive electrode active substance with a conducting agent such as acetylene black or carbon black and a binder such as polytetrafluoroethylene (PTFE), polyvinylidene fluoride (PVDF), styrene and butadiene copolymer (SBR), acrylonitrile and butadiene copolymer (NBR), carboxymethyl cellulose (CMC) or ethylene-propylene diene terpolymer, adding a high boiling solvent such as 1-methyl-2-pyrrolidone thereto and mixing to obtain a positive electrode mix, coating the positive electrode mix onto aluminum foil or stainless steel lass plate and the like of a current collector, drying and pressure molding followed by heat-treating in a vacuum for about 2 hours at a temperature of about 50 to 250° C.

One type or a combination of two or more types of lithium metal, lithium alloy or carbon material (graphite such as artificial graphite or natural graphite), tin, tin compound, silicon or silicon compound and the like capable of occluding and releasing lithium can be used as a negative electrode active material.

Among these, highly crystalline carbon materials are used preferably in terms of their ability to occlude and release lithium ions, and carbon materials having a graphite crystal structure in which the interplanar distance ($d_{002}$) of lattice plane (002) is 0.340 nm or less and particularly 0.335 to 0.337 nm are used particularly preferably. In addition, a highly crystalline carbon material may be coated with a lowly crystalline material. Although the use of a highly crystalline material easily reacts with electrolytic solution during charging, this reaction can be inhibited in the lithium secondary battery as claimed in the disclosed embodiments.

Tin, tin compounds, silicon and silicon compounds are preferable since they are able to increase battery capacity.

The negative electrode can be fabricated by obtaining a negative electrode mix by using a conducting agent, binder and highly boiling solvent and mixing in the same manner as the fabrication of the positive electrode as previously described, followed by coating this negative electrode mix onto a copper foil and the like of a current collector, drying, pressure molding and heat-treating in a vacuum for about 2 hours at a temperature of about 50 to 250° C.

A single-layer or laminated porous film of a polyolefin such as polypropylene or polyethylene, a woven fabric or a non-woven fabric and the like can be used as a battery separator.

There are no particular limitations on the structure of the lithium secondary battery as claimed in the disclosed embodiments, and a coin shaped battery, cylindrical battery, square shaped battery or laminate type battery and the like can be applied.

The lithium secondary battery in the disclosed embodiments has superior cycle performance over a long period of time in the case of a charge cutoff voltage of 4.2 V or more, and particularly in the case of a charge cutoff voltage of 4.3 V or more, and demonstrates satisfactory charge performance even at a charge cutoff voltage of 4.4 V. The discharge cutoff voltage can be 2.5 V or more, and even 2.8 V or more. Although there are no particular limitations on current value, the lithium secondary battery of the disclosed embodiments is normally used a constant current discharge of 0.1 to 3 C. In addition, the lithium secondary battery in the disclosed embodiments is capable of charging and discharging at −40 to 100° C. and preferably 0 to 80° C.

The di-tert-butylphenyl alkylsulfonate compound, di-tert-butylphenyl arylsulfonate compound, tert-butylphenyl alylsulfonate compound and tert-butylphenyl arylsulfonate compound of the disclosed embodiments can be synthesized according to, but not limited to, the methods described below.

Method 1

The above compounds can be obtained by an esterification reaction of di-tert-butylphenol or tert-butylphenol with an alkanesulfonyl halide, arylsulfonyl halide, alkanesulfonic anhydride or arylsulfonic anhydride in the presence or absence of solvent and in the presence of base.

Method 2

Di-tert-butylphenol or tert-butylphenol is converted to an alkali metal salt and reacted in an esterification reaction with sulfonyl halide in the presence or absence of solvent.

The amount of alkanesulfonyl halide, arylsulfonyl halide, alkanesulfonic acid anhydride or arylsulfonic acid anhydride reacted with the di-tert-butylphenol or tert-butylphenol in Method 1 is preferably 0.9 to 10 mol, more preferably 1 to 3 mol and most preferably 1 to 1.5 mol based on 1 mol of di-tert-butylphenol or 1 mol of tert-butylphenol.

Although examples of alkanesulfonyl halide used in Method 1 of the disclosed embodiments include methanesulfonyl chloride, ethanesulfonyl chloride, trifluoromethanesulfonyl chloride, methanesulfonyl bromide, ethanesulfonyl bromide and trifluoromethanesulfonyl bromide, industrially inexpensive sulfonyl chlorides such as methanesulfonyl chloride, ethanesulfonyl chloride or trifluoromethanesulfonyl chloride are preferable.

In addition, although examples of arylsulfonyl halides include benzenesulfonyl chloride, p-toluenesulfonyl chloride, benzenesulfonyl bromide and p-toluenesulfonyl bromide, industrially inexpensive benzenesulfonyl chloride or p-toluenesulfonyl chloride is preferable.

In addition, examples of alkanesulfonic anhydrides include methanesulfonic anhydride, ethanesulfonic anhydride and trifluoromethanesulfonic anhydride.

In addition, examples of arylsulfonic anhydrides include benzenesulfonic anhydride and p-toluenesulfonic anhydride.

Although there are no particular limitations on the solvent used in Method 1 provided it is inert in the reaction, examples of solvents include aliphatic hydrocarbons such as hexane or heptane, halogenated hydrocarbons such as dichloroethane or dichloropropane, aromatic hydrocarbons such as toluene or xylene, halogenated aromatic hydrocarbons such as chlorobenzene or fluorobenzene, ethers such as diethyl ether, nitriles such as acetonitrile or propionitrile, amides such as N,N-dimethylformamide, sulfoxides such as dimethylsulfoxide, nitro compounds such as nitromethane or nitroethane, esters such as ethyl acetate or dimethyl carbonate, and mixtures thereof. Use of toluene or xylene is particularly preferred. The amount of the solvent used is preferably 0 to 30 parts by weight and more preferably 1 to 15 parts by weight based on 1 part by weight of di-tert-butylphenol or 1 part by weight of tert-butylphenol.

An inorganic base or an organic base can be used for the base used in Method 1. These can be used alone or as a mixture. Examples of inorganic bases used include potassium carbonate, sodium carbonate, calcium hydroxide and calcium oxide. Examples of organic bases used include linear or branched aliphatic tertiary amines and mono- or multi-substituted pyrroles, pyrrolidones, imidazoles, imidazolidinones, pyridines, pyrimidines, quinolines and N,N-dialkylcarboxyamides, with trialkylamines such as trimethylamine, triethylamine, tripropylamine, tributylamine or ethyldiisopropylamine, pyridine, N-methylpyrrolidone, N,N-dimethylacetoamide, N,N-dimethylaminopyridine and 1,3-dimethylimidazolidinone being particularly preferable. The amount of base used is preferably 0.8 to 5 mol and more preferably 1 to 3 mol based on 1 mol of di-tert-butylphenol or 1 mol of tert-butylphenol, while 1 to 1.5 mol is particularly preferably due to inhibiting the formation of by-products.

In the reaction of Method 1 between any one type of alkanesulfonyl halide, arylsulfonyl halide, alkanesulfonic acid anhydride or arylsulfonic acid anhydride and di-tert-butylphenol or tert-butylphenol, the lower limit of the reaction temperature is preferably −20° C. or higher, and more preferably −10° C. or higher to prevent a decrease in reactivity. In addition, the upper limit of the reaction temperature is preferably 80° C. or lower, and more preferably 60° C. or lower since a temperature in excess thereof allows side reactions and decomposition of products to proceed easily. In addition, although varying according to the reaction temperature and reaction scale, the reaction time is preferably 0.1 to 12 hours and more preferably 0.2 to 6 hours since an excessively short reaction time causes unreacted substances to remain, while an excessively long reaction time results in the risk of decomposition of products and the occurrence of side reactions.

Examples of alkali metals reacted with the di-tert-butylphenol or tert-butylphenol in Method 2 include lithium, sodium, potassium and rubidium. Examples of forms in which the alkali metal is used include simple metals, metal hydrides and metal hydroxides, and simple metals and metal hydrides can be used preferably due to their high reactivity with di-tert-butylphenol or tert-butylphenol. If the amount of alkali metal used per 1 mol of di-tert-butylphenol or 1 mol of tert-butylphenol is less than 0.8 mol, the amount of di-tert-butylphenol or tert-butylphenol remaining increases, the amount of target ester produced and productivity decrease. In addition, since there is increased likelihood of the occurrence of side reactions in which residual alkali metal reacts with sulfonyl halide if the amount of alkali metal used exceeds 2 mol, the amount of alkali metal used is preferably 0.8 to 2 mol and more preferably 1 to 1.2 mol based on the di-tert-butylphenol or tert-butylphenol.

Although examples of sulfonyl halides used in Method 2 include alkanesulfonyl halides such as methanesulfonyl chloride, ethanesulfonyl chloride, trifluoromethanesulfonyl chloride, methanesulfonyl bromide, ethanesulfonyl bromide or trifluoromethanesulfonyl bromide, and arylsulfonyl halides such as benzenesulfonyl chloride, p-toluenesulfonyl chloride, benzenesulfonyl bromide or p-toluenesulfonyl bromide, industrially inexpensive sulfonyl chlorides such as methanesulfonyl chloride, ethanesulfonyl chloride, trifluoromethanesulfonyl chloride, benzenesulfonyl chloride or p-toluenesulfonyl chloride are preferable.

Although there are no particular limitations on the solvent used in Method 2 provided it is inert in the reaction, examples of solvents include aliphatic hydrocarbons such as hexane, heptane or cyclohexane, aromatic hydrocarbons such as toluene or xylene, ethers such as diethyl ether, diisopropyl ether, tetrahydrofuran, dioxane, dimethoxyethane, diethoxyethane, diglyme or triglyme, nitro compounds such as nitromethane or nitroethane, and mixtures thereof. The amount of the solvent used is preferably 0 to 30 parts by weight and more preferably 0.5 to 10 parts by weight based on 1 part by weight of di-tert-butylphenol or 1 part by weight of tert-butylphenol.

In the reaction of Method 2 between sulfonyl halide and di-tert-butylphenol alkali metal salt or between sulfonyl halide and tert-butylphenol alkali metal salt, the lower limit of the reaction temperature is preferably −70° C. or higher, and more preferably −20° C. or higher to prevent a decrease in reactivity. In addition, the upper limit of the reaction temperature is preferably 80° C. or lower, and more preferably 60° C. or lower. If the reaction temperature exceeds 80° C., side reactions and decomposition of products proceed easily. In addition, although varying according to the reaction temperature and reaction scale, the reaction time is preferably 0.1 to 12 hours and more preferably 0.2 to 6 hours since an excessively short reaction time causes unreacted substances to remain, while conversely an excessively long reaction time results in the risk of decomposition of products and the occurrence of side reactions. The reaction pressure is within the range of 0.1 to 10 atm and preferably within the range of 0.5 to 5 atm.

In the esterification reaction of Method 2 between sulfonyl halide and di-tert-butylphenol alkali metal salt or between sulfonyl halide and tert-butylphenol alkali metal salt, the amount of sulfonyl halide used is preferably 0.9 to 5 mol, more preferably 1 to 3 mol and most preferably 1 to 1.5 mol based on 1 mol of di-tert-butylphenol alkali metal salt or 1 mol of tert-butylphenol alkali metal salt.

EXAMPLES

Examples are given below to more fully illustrate the disclosed embodiments, and should not be construed as limiting the disclosed embodiments.

It will be apparent to those skilled in the art that various modifications and variations can be made in the disclosed embodiments and specific examples provided herein without departing from the spirit or scope of the disclosed embodiments. Thus, it is intended that the disclosed embodiments covers the modifications and variations of this disclosed embodiments that come within the scope of any claims and their equivalents The following examples are for illustrative purposes only and are not intended, nor should they be interpreted to, limit the scope of the disclosed embodiments.

Synthesis Example 1

Synthesis of 2,4-di-tert-butylphenyl Methanesulfonate (Compound 1)

21.00 g (0.102 mol) of 2,4-di-tert-butylphenol and 11.84 g (0.117 mol) of triethylamine were dissolved in 200 mL of toluene followed by dropping in 12.24 g (0.107 mol) of methanesulfonyl chloride over the course of 30 minutes at 10° C. Following completion of dropping, the mixture was stirred for 2 hours at 25° C. and the 2,4-di-tert-butylphenol was confirmed to no longer be present. The reaction liquid was placed in 3% aqueous hydrochloric acid solution and following separation of the organic layer, was washed once with saturated aqueous $NaHCO_3$ solution and twice with saturated brine followed by drying with $MgSO_4$ and concentrating. The resulting crude crystals were purified by crystallization with n-heptane to obtain 25.8 g (yield: 90%) of 2,4-di-tert-butylphenyl methanesulfonate (white crystals, melting point: 63° C.).

The resulting 2,4-di-tert-butylphenyl methanesulfonate was analyzed by $^1$H-NMR, $^{13}$C-NMR, IR and mass spectrometry to confirm the structure thereof. The results are indicated below.

(1) $^1$H-NMR (300 MHz, $CDCl_3$): δ=7.5-7.2 (m, 3H), 3.2 (s, 3H), 1.4 (s, 9H), 1.3 (s, 9H)

(2) $^{13}$C-NMR (75 MHz, $CDCl_3$): δ=148.9, 146.6, 139.8, 125.1, 124.2, 119.9, 39.1, 34.9, 34.7, 31.4, 30.5

(3) IR (KBr method): 2962, 1490, 1350, 1194, 1167, 1078, 974, 906, 866, 832, 592 $cm^{-1}$ (4) Mass spectrometry: MS (EI) m/z (%)=284(25) [M$^+$]: 269(82), 190 (15), 175 (14), 149 (18), 57 (100), 41 (14)

Synthesis Example 2

Synthesis of 2,4-di-tert-butylphenyl Ethanesulfonate (Compound 2)

8.04 g (0.0389 mol) of 2,4-di-tert-butylphenol and 4.13 g (0.0408 mol) of triethylamine were dissolved in 15 mL of toluene followed by dropping in 5.01 g (0.0389 mol) of ethanesulfonyl chloride over the course of 30 minutes at 10° C. Following completion of dropping, the mixture was stirred for 2 hours at 25° C. and the 2,4-di-tert-butylphenol was confirmed to no longer be present. The reaction liquid was placed in 3% aqueous hydrochloric acid solution and following separation of the organic layer, was washed once with saturated aqueous $NaHCO_3$ solution and twice with saturated brine followed by drying with $MgSO_4$ and concentrating. The resulting crude crystals were purified by crystallization with n-heptane to obtain 8.14 g (yield: 70%) of 2,4-di-tert-butylphenyl ethanesulfonate (white crystals, melting point: 76° C.).

The resulting 2,4-di-tert-butylphenyl ethanesulfonate was analyzed by $^1$H-NMR, $^{13}$C-NMR, IR and mass spectrometry to confirm the structure thereof. The results are indicated below.

(1) $^1$H-NMR (300 MHz, $CDCl_3$): δ=7.5-7.4 (m, 2H), 7.3-7.2 (m, 1H), 3.39 (q, J=7.56 Hz, 2H), 1.58 (t, J=7.56 Hz, 3H), 1.41 (s, 9H), 1.31 (s, 9H)

(2) $^{13}$C-NMR (75 MHz, CDCl$_3$): δ=148.6, 146.5, 139.8, 125.0, 124.2, 120.1, 47.1, 34.9, 34.7, 31.4 (3C), 30.5 (3C), 8.1

(3) IR (KBr method): 3435, 2972, 2817, 1494, 1347, 1187, 1157, 1077, 904, 856, 834, 787, 586 cm$^{-1}$ (4) Mass spectrometry: MS (EI) m/z (%)=298 (23) [M$^+$]: 283 (53), 227 (7), 191 (16), 149 (30), 121 (5), 91 (5), 57 (100), 41 (11)

Synthesis Example 3

Synthesis of 2,4-di-tert-butylphenyl Trifluoro methanesulfonate (Compound 3)

26.05 g (0.126 mol) of 2,4-di-tert-butylphenol and 20.07 g (0.254 mol) of pyridine were dissolved in 200 mL of toluene followed by dropping in 39.20 g (0.139 mol) of trifluoromethanesulfonic acid anhydride over the course of 30 minutes at 10° C. Following completion of dropping, the mixture was stirred for 2 hours at 25° C. and the 2,4-di-tert-butylphenol was confirmed to no longer be present. The reaction liquid was placed in 3% aqueous hydrochloric acid solution and following separation of the organic layer, was washed once with saturated aqueous NaHCO$_3$ solution and twice with saturated brine followed by drying with MgSO$_4$ and concentrating. The resulting crude product was purified by vacuum distillation to obtain 29.05 g (yield: 68%) of 2,4-di-tert-butylphenyl trifluoromethanesulfonate (yellow oily substance, boiling point: 103° C./1.5 Torr).

The resulting 2,4-di-tert-butylphenyl trifluoromethanesulfonate was analyzed by $^1$H-NMR, $^{13}$C-NMR, IR and mass spectrometry to confirm the structure thereof. The results are indicated below.

(1) $^1$H-NMR (300 MHz, CDCl$_3$): δ=7.2-7.1 (m, 3H), 1.40 (s, 9H), 1.28 (s, 9H)

(2) $^{13}$C-NMR (75 MHz, CDCl$_3$): δ=147.2, 143.1, 136.7, 123.2, 122.8, 120.3, 114.0-123.5 (J$_{C-F}$=319.0 Hz), 35.4, 34.4, 31.4 (3C), 29.4 (3C)

(3) IR (KBr method): 3534, 2962, 2908, 2870, 1575, 1481, 1406, 1285, 1252, 1204, 1180, 867, 852, 766 cm$^{-1}$ (4) Mass spectrometry: MS (EI) m/z (%)=338 (27) [M$^+$]: 283 (11), 225 (19), 190 (14), 57 (100), 41 (20)

Synthesis Example 4

Synthesis of 2,4-di-tert-butylphenyl p-toluenesulfonate (Compound 4)

1.02 g (0.026 mol) of 60% oil-dispersed sodium hydride were dissolved in 20 mL of ether and cooled to 5° C. 20 mL of an ether solution containing 5.00 g (0.024 mol) of 2,4-di-tert-butylphenol were dropped in over the course of 15 minutes at 5° C. and stirred for 30 minutes followed by dropping in 20 mL of a toluene solution containing 4.16 g (0.022 mol) of p-toluenesulfonyl chloride over the course of 20 minutes, stirring for 30 minutes at 25° C. and confirming the 2,4-di-tert-butylphenol to no longer be present. Following completion of the reaction, water was added and the organic layer was extracted with ethyl acetate followed by washing twice with saturated aqueous NaHCO$_3$ solution and once with saturated brine, drying with MgSO$_4$ and concentrating. The resulting crystals were purified by crystallizing with n-hexane to obtain 3.0 g (yield: 38%) of 2,4-di-tert-butylphenyl p-toluenesulfonate (white crystals, melting point: 81° C.).

The resulting 2,4-di-tert-butylphenyl p-toluenesulfonate was analyzed by $^1$H-NMR, $^{13}$C-NMR, IR and mass spectrometry to confirm the structure thereof. The results are indicated below.

(1) $^1$H-NMR (300 MHz, CDCl$_3$): δ=7.9-7.8 (m, 2H), 7.4-7.3 (m, 3H), 7.2-7.1 (m, 2H), 2.45 (s, 3H), 1.35 (s, 9H), 1.28 (s, 9H)

(2) $^{13}$C-NMR (75 MHz, CDCl$_3$): δ=148.5, 147.3, 145.0, 140.1, 134.9, 129.9, 128.0, 124.9, 123.9, 119.8, 34.8, 34.6, 31.4 (3C), 30.5 (3C), 21.7

(3) IR (KBr method): 3425, 3002, 1598, 1490, 1397, 1372, 1194, 1172, 1074, 853, 828, 814, 771, 705, 672, 595 cm$^{-1}$ (4) Mass spectrometry: MS (EI) m/z (%)=360 (29) [M$^+$]: 345 (23), 289 (4), 149 (10), 91 (23), 57 (100), 41 (16)

Synthesis Example 5

Synthesis of 2,6-di-tert-butylphenyl Methanesulfonate (Compound 5)

50 mL of a tetrahydrofuran (THF) solution containing 10.00 g (0.049 mol) of 2,6-di-tert-butylphenol were dropped into 100 mL of a THF suspension of 2.03 g (0.051 mol) of 60% oil-dispersed sodium hydride at 0° C. followed by stirring for 1 hour at the same temperature to prepare sodium 2,6-di-tertbutylphenoxide. 5.81 g (0.051 mol) of 1,3-dimethyl-2-imidazolidinone were added to this solution, and after stirring for 30 minutes at 0° C., 5.83 g (0.051 mol) of methanesulfonyl chloride were dropped in followed by stirring for 2 hours at 25° C. The reaction liquid was placed in 30% aqueous hydrochloric acid solution and following separation of the organic layer, the organic layer was washed once with 1 N aqueous NaOH solution and twice with water followed by drying with MgSO$_4$ and concentrating. The resulting crude crystals were purified by crystallization with a 1/1 (volumetric ratio) mixture of n-hexane and isopropanol to obtain 4.8 g (yield: 35%) of 2,6-di-tert-butylphenyl methanesulfonate (white crystals, melting point: 83° C.).

The resulting 2,6-di-tert-butylphenyl methanesulfonate was analyzed by $^1$H-NMR, $^{13}$C-NMR, IR and mass spectrometry to confirm the structure thereof.

(1) $^1$H-NMR (300 MHz, CDCl$_3$): δ=7.9-7.1 (m, 3H), 3.2 (s, 3H), 1.5 (s, 18H)

(2) $^{13}$C-NMR (75 MHz, CDCl$_3$): δ=145.0, 141.5, 128.0, 125.9, 38.6, 37.0, 32.7

(3) IR (KBr method): 2986, 2957, 1412, 1347, 1324, 1186, 1162, 1096, 974, 862, 822, 763, 570, 540, 503 cm$^{-1}$ (4) Mass spectrometry: MS (EI) m/z (%)=284 (11) [M$^+$]: 269 (10), 175 (3), 149 (23), 57 (100), 41 (12), 29 (7)

Synthesis Example 6

Synthesis of 3,5-di-tert-butylphenyl Methanesulfonate (Compound 6)

2.50 g (0.012 mol) of 3,5-di-tert-butylphenol and 1.27 g (0.013 mol) of triethylamine were dissolved in 15 mL of toluene followed by dropping in 1.45 g (0.013 mol) of methanesulfonyl chloride over the course of 10 minutes at 5° C. Following completion of dropping, the mixture was stirred for 3 hours at 25° C. and the 3,5-di-tert-butylphenol was confirmed to no longer be present. The reaction liquid was placed in ice water and following separation of the organic layer, was washed twice with saturated brine followed by drying with MgSO$_4$ and concentrating to obtain 3.21 g (yield: 98%) of 3,5-di-tert-butylphenyl methanesulfonate. A purified product crystallized with n-hexane (white crystals, melting point: 76° C.) was used in a battery test.

The resulting 3,5-di-tert-butylphenyl methanesulfonate was analyzed by $^1$H-NMR, IR and mass spectrometry to confirm the structure thereof. The results are indicated below.

(1) $^1$H-NMR (300 MHz, CDCl$_3$): δ=7.37 (t, J=1.7 Hz, 1H), 7.09 (d, J=1.7 Hz, 2H), 3.13 (s, 3H), 1.32 (s, 18H)

(2) IR (KBr method): 2956, 1613, 1586, 1478, 1421, 1366, 1190, 1165, 968, 949, 875, 829, 799, 735, 706 cm$^{-1}$ (3) Mass spectrometry: MS (EI) m/z (%)=284 (12) [M$^+$]: 269 (100), 147 (8), 57 (21)

Synthesis Example 7

Synthesis of 3,5-di-tert-butylphenyl Ethanesulfonate (Compound 7)

2.50 g (0.012 mol) of 3,5-di-tert-butylphenol and 1.27 g (0.013 mol) of triethylamine were dissolved in 15 mL of toluene followed by dropping in 1.62 g (0.013 mol) of ethanesulfonyl chloride over the course of 10 minutes at 5° C. Following completion of dropping, the mixture was stirred for 2 hours at 25° C. and the 3,5-di-tert-butylphenol was confirmed to no longer be present. The reaction liquid was placed in ice water and following separation of the organic layer, was washed twice with saturated brine followed by drying with MgSO$_4$ and concentrating to obtain 3.27 g (yield: 91%) of 3,5-di-tert-butylphenyl ethanesulfonate. A purified product crystallized with n-hexane (white crystals, melting point: 52° C.) was used in a battery test.

The resulting 3,5-di-tert-butylphenyl ethanesulfonate was analyzed by $^1$H-NMR, IR and mass spectrometry to confirm the structure thereof. The results are indicated below.

(1) $^1$H-NMR (300 MHz, CDCl$_3$): δ=7.35 (t, J=1.7 Hz, 1H), 7.08 (d, J=1.7 Hz, 2H), 3.27 (q, J=7.6 Hz, 2H), 1.54 (t, J=7.6 Hz, 3H), 1.32 (s, 18H)

(2) IR (KBr method): 2967, 1609, 1584, 1344, 1296, 1182, 1161, 946, 933, 872, 827, 793, 768, 708 cm$^{-1}$ (3) Mass spectrometry: MS (EI) m/z (%)=298(14) [M$^+$]: 283 (100), 147 (8), 57 (46)

Synthesis Example 8

Synthesis of 3-tert-butylphenyl Methanesulfonate (Compound 8)

8.00 g (53.3 mol) of 3-tert-butylphenol and 5.93 g (58.6 mol) of triethylamine were dissolved in 80 mL of toluene followed by dropping in 6.71 g (58.6 mol) of methanesulfonyl chloride over the course of 10 minutes at 10° C. followed by stirring for 10 minutes at 25° C. and confirming the 3-tert-butylphenol to no longer be present by gas chromatography. The reaction liquid was placed in water and following separation of the organic layer, was washed three times with water, once with saturated aqueous NaHCO$_3$ solution and once with saturated brine followed by drying with MgSO$_4$, concentrating and purifying the resulting residue by vacuum distillation to obtain 10.7 g (yield: 88%) of 3-tert-butylphenyl methanesulfonate.

The resulting 3-tert-butylphenyl methanesulfonate was analyzed by $^1$H-NMR, $^{13}$C-NMR and mass spectrometry to confirm the structure thereof. The results are indicated below.

(1) $^1$H-NMR (300 MHz, CDCl$_3$): δ=7.35-7.08 (m, 4H), 3.12 (s, 3H), 1.32 (s, 9H)

(2) $^{13}$C-NMR (75 MHz, CDCl$_3$): δ=153.9, 149.3, 129.4, 124.3, 119.1, 118.7, 37.2, 34.9, 31.1 (3C)

(3) Mass spectrometry: MS (EI) m/z (%)=228(21), 213 (100), 185(10), 134(13), 91(15), 41(6)

Synthesis Example 9

Synthesis of 2-tert-butylphenyl Ethanesulfonate (Compound 9)

8.00 g (53.3 mol) of 2-tert-butylphenol and 5.93 g (58.6 mol) of triethylamine were dissolved in 80 mL of toluene followed by dropping in 7.53 g (58.6 mol) of ethanesulfonyl chloride over the course of 10 minutes at 10° C. followed by stirring for 10 minutes at 25° C. and confirming the 2-tert-butylphenol to no longer be present by gas chromatography. The reaction liquid was placed in water and following separation of the organic layer, was washed three times with water, once with saturated aqueous NaHCO$_3$ solution and once with saturated brine followed by drying with MgSO$_4$, concentrating and purifying the resulting residue by vacuum distillation to obtain 11.93 g (yield: 92%) of 2-tert-butylphenyl ethanesulfonate.

The resulting 2-tert-butylphenyl ethanesulfonate was analyzed by $^1$H-NMR, $^{13}$C-NMR and mass spectrometry to confirm the structure thereof. The results are indicated below.

(1) $^1$H-NMR (300 MHz, CDCl$_3$): δ=7.54-7.16 (m, 4H), 3.43 (q, J=7.5 Hz, 2H), 1.60 (t, J=7.5 Hz, 3H), 1.41 (s, 9H)

(2) $^{13}$C-NMR (75 MHz, CDCl$_3$): δ=148.8, 140.7, 128.0, 127.3, 126.0, 120.7, 47.1, 34.7, 30.4 (3C), 8.1

(3) Mass spectrometry: MS (EI) m/z (%)=242(47), 227 (100), 163(8), 134(70), 91(34), 29(31)

Synthesis Example 10

Synthesis of 3-tert-butylphenyl Ethanesulfonate (Compound 10)

8.00 g (53.3 mol) of 3-tert-butylphenol and 5.93 g (58.6 mol) of triethylamine were dissolved in 80 mL of toluene followed by dropping in 7.53 g (58.6 mol) of ethanesulfonyl chloride over the course of 10 minutes at 10° C. followed by stirring for 10 minutes at 25° C. and confirming the 3-tert-butylphenol to no longer be present by gas chromatography. The reaction liquid was placed in water and following separation of the organic layer, was washed three times with water, once with saturated aqueous NaHCO$_3$ solution and once with saturated brine followed by drying with MgSO$_4$, concentrating and purifying the resulting residue by vacuum distillation to obtain 12.02 g (yield: 93%) of 3-tert-butylphenyl ethanesulfonate.

The resulting 3-tert-butylphenyl ethanesulfonate was analyzed by $^1$H-NMR, $^{13}$C-NMR and mass spectrometry to confirm the structure thereof. The results are indicated below.

(1) $^1$H-NMR (300 MHz, CDCl$_3$): δ=7.33-7.06 (m, 4H), 3.30 (q, J=7.5 Hz, 2H), 1.55 (t, J=7.5 Hz, 3H), 1.32 (s, 9H)

(2) $^{13}$C-NMR (75 MHz, CDCl$_3$): δ=153.8, 149.1, 129.3, 124.1, 119.1, 118.7, 44.9, 34.8, 31.1 (3C), 8.2

(3) Mass spectrometry: MS (EI) m/z (%)=242 (24), 227 (100), 199 (4), 163 (5), 135 (27), 91 (13), 29 (19)

The following are non-limiting examples using the electrolytic solution of the disclosed embodiments.

Example 1

Preparation of Electrolytic Solution

LiPF$_6$ and LiN(SO$_2$CF$_3$)$_2$ were dissolved to a concentration of 0.95 M and 0.05 M, respectively, in a nonaqueous solvent mixture including or consisting of ethylene carbonate (EC), vinylene carbonate (VC), methyl ethyl carbonate (MEC) and diethyl carbonate (DEC) prepared at a ratio of 28:2:35:35 (volumetric ratio) followed by the addition of an added compound in the form of 2,4-di-tert-butylphenyl trifluoromethanesulfonate at 0.1% by weight relative to a nonaqueous electrolytic solution to prepare a nonaqueous electrolytic solution.

Fabrication of Lithium Ion Secondary Battery $LiCoO_2$ (positive electrode active material) at a ratio of 92% by weight, acetylene black (conducting agent) at a ratio of 3% by weight and polyvinylidene fluoride (binder) at a ratio of 5% by weight were mixed followed by the addition of a solvent in the form of 1-methyl-2-pyrrolidone and mixing therewith and then coating the mixture onto an aluminum foil current collector, drying and pressure molding to prepare a positive electrode sheet by stamping out to a diameter of 16 mmφ. Artificial graphite (negative electrode active material) at a ratio of 95% by weight and polyvinylidene fluoride (binder) at a ratio of 5% by weight were then mixed followed by the addition of solvent in the form of 1-methyl-2-pyrrolidone and mixing therewith and then coating the mixture onto a copper foil current collector, drying and pressure molding to prepare a negative electrode sheet by stamping out to a diameter of 16 mmφ. The positive electrode sheet, a microporous polyethylene film separator and the negative electrode sheet were laminated in that order followed by housing in a size code 2032 coin cell can, injecting the prepared electrolytic solution, and fastening a cover to the cell can through a polypropylene gasket to fabricate a battery.

Measurement of Battery Characteristics

The resulting coin shaped battery was charged for 5 hours to a cutoff voltage of 4.2 V at a constant current of 2 mA and constant voltage at room temperature (25° C.) and then discharging to a cutoff voltage of 2.7 V at a constant current of 2 mA, and repeating this charging and discharging for 100 cycles. The discharge capacity during the 100th cycle was measured, and the discharge capacity retention (%) after 100 cycles was determined according to the following formula based on a value of 100% for the initial discharge capacity. The capacity maintenance rate was 87% where the capacity maintenance rate (%)=(discharge capacity after 100 cycles/discharge capacity of 1st cycle)×100.

Examples 2 to 5

Coin shaped batteries were fabricated and measured for battery properties by preparing nonaqueous electrolytic solutions in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared at a ratio of 28:2:35:35 (volumetric ratio), and adding 2,4-di-tert-butylphenyl methanesulfonate at 0.1% by weight, 1% by weight, 5% by weight and 10% by weight, respectively, relative to the nonaqueous electrolytic solution instead of the 2,4-di-tert-butylphenyl trifluoromethanesulfonate used in Example 1. The results are shown in Table 1.

Example 6

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2,4-di-tert-butylphenyl ethanesulfonate at 1% by weight relative to the nonaqueous electrolytic solution instead of 2,4-di-tert-butylphenyl trifluoromethanesulfonate used in Example 1. The results are shown in Table 1.

Example 7

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2,4-di-tert-butylphenyl benzenesulfonate at 1% by weight relative to the nonaqueous electrolytic solution instead of 2,4-di-tert-butylphenyl trifluoromethanesulfonate used in Example 1. The results are shown in Table 1.

Example 8

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2,4-di-tert-butylphenyl p-toluenesulfonate at 1% by weight relative to the nonaqueous electrolytic solution instead of 2,4-di-tert-butylphenyl trifluoromethanesulfonate used in Example 1. The results are shown in Table 1.

Comparative Example 1

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), but not adding the 2,4-di-tert-butylphenyl trifluoromethanesulfonate used in Example 1. The results are shown in Table 1.

Comparative Example 2

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding phenyl trifluoromethanesulfonate at 0.1% by weight relative to the nonaqueous electrolytic solution instead of the 2,4-di-tert-butylphenyl trifluoromethanesulfonate used in Example 1. The results are shown in Table 1.

Comparative Example 3

A coin shaped battery was fabricated and measured for battery properties by preparing a nonaqueous electrolytic solution in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2,4-di-methylphenyl trifluoromethanesulfonate at 0.1% by weight relative to the nonaqueous electrolytic solution instead of the 2,4-di-tert-butylphenyl trifluoromethanesulfonate used in Example 1. The results are shown in Table 1.

Example 14

A coin shaped battery was fabricated and measured for battery properties by preparing a nonaqueous electrolytic solution in the same manner as Example 1 with the exception of using Si for the negative electrode active material instead of artificial graphite, mixing Si (negative electrode active material) at a ratio of 75% by weight, artificial graphite (conducting agent) at a ratio of 10% by weight, acetylene black (conducting agent) at a ratio of 10% by weight and polyvinylidene fluoride (binder) at a ratio of 5% by weight, adding a solvent in the form of a 1-methyl-2-pyrrolidone and mixing therewith, coating the mixture onto a copper foil current collector, drying and pressure molding to fabricate a positive electrode sheet in the form of a strip by cutting to a prescribed size, dissolving $LiPF_6$ to a concentration of 0.95 M and $LiBF_4$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2,4-di-tert-butylphenyl methanesulfonate at 2% by weight relative to the nonaqueous electrolytic solution instead of adding the 2,4-di-tert-butylphenyl trifluoromethanesulfonate used in Example 1. The results are shown in Table 3.

Comparative Example 4

A coin shaped battery was fabricated and measured for battery properties by preparing a nonaqueous electrolytic solution in the same manner as Example 14 with the exception of not adding the 2,4-di-tert-butylphenyl methanesulfonate used in Example 14. The results are shown in Table 3.

TABLE 1

|  | Added Compound | Added Amount (wt %) | Capacity Retention After 100 Cycle (%) |
|---|---|---|---|
| Example 1 | 2,4-di-tert-butylphenyl trifluoromethanesulfonate | 0.1 | 87 |
| Example 2 | 2,4-di-tert-butylphenyl methanesulfonate | 0.1 | 89 |
| Example 3 | 2,4-di-tert-butylphenyl methanesulfonate | 1 | 92 |
| Example 4 | 2,4-di-tert-butylphenyl methanesulfonate | 5 | 90 |
| Example 5 | 2,4-di-tert-butylphenyl methanesulfonate | 10 | 89 |
| Example 6 | 2,4-di-tert-butylphenyl ethanesulfonate | 1 | 91 |
| Example 7 | 2,4-di-tert-butylphenyl benzenesulfonate | 1 | 90 |
| Example 8 | 2,4-di-tert-butylphenyl p-toluenesulfonate | 1 | 89 |
| Comp. Ex. 1 | None | — | 82 |
| Comp. Ex. 2 | Phenyl trifluoromethanesulfonate | 0.1 | 82 |
| Comp. Ex. 3 | 2,4-di-methylphenyl trifluoromethanesulfonate | 0.1 | 80 |

Examples 9 to 13

Coin shaped batteries were fabricated and measured for battery properties by preparing nonaqueous electrolytic solutions in the same manner as Example 1 with the exception of dissolving $LiPF_6$ to a concentration of 0.95 M and $LiN(SO_2CF_3)_2$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared at a ratio of 28:2:35:35 (volumetric ratio), and respectively adding 2,6-di-tert-butylphenyl methanesulfonate, 2,6-di-tert-butylphenyl ethanesulfonate, 3,5-di-tert-butylphenyl methanesulfonate, 3,5-di-tert-butylphenyl ethanesulfonate and 2,5-di-tert-butylphenyl methanesulfonate at 1% by weight each relative to the nonaqueous electrolytic solution instead of the 2,4-di-tert-butylphenyl trifluoromethanesulfonate used in Example 1. The results are shown in Table 2.

TABLE 2

|  | Added Compound | Added Amount (wt %) | Capacity Retention After 100 Cycle (%) |
|---|---|---|---|
| Example 9 | 2,6-di-tert-butylphenyl methanesulfonate | 1 | 91 |
| Example 10 | 2,6-di-tert-butylphenyl ethanesulfonate | 1 | 91 |
| Example 11 | 3,5-di-tert-butylphenyl methanesulfonate | 1 | 89 |
| Example 12 | 3,5-di-tert-butylphenyl ethanesulfonate | 1 | 88 |
| Example 13 | 2,5-di-tert-butylphenyl methanesulfonate | 1 | 89 |

TABLE 3

| | Added Compound | Amount Added (wt %) | Capacity Retention After 100 Cycle (%) |
|---|---|---|---|
| Example 14 | 2,4-di-tert-butylphenyl methanesulfonate | 2 | 77 |
| Comp. Ex. 4 | None | — | 39 |

Example 15

A coin shaped battery was fabricated and measured for battery properties by preparing a nonaqueous electrolytic solution in the same manner as Example 1 with the exception of using LiFePO$_4$ for the positive electrode active material instead of LiCoO$_2$, mixing LiFePO$_4$ (positive electrode active material) at a ratio of 90% by weight, acetylene black (conducting agent) at a ratio of 5% by weight and polyvinylidene fluoride (binder) at a ratio of 5% by weight, adding a solvent in the form of a 1-methyl-2-pyrrolidone and mixing therewith, coating the mixture onto an aluminum foil current collector, drying and pressure molding to fabricate a positive electrode sheet in the form of a strip by cutting to a prescribed size, mixing graphite coated with lowly crystalline carbon (negative electrode active material) at a ratio of 95% by weight and polyvinylidene fluoride (binder) at a ratio of 5% by weight, adding a solvent in the form of 1-methyl-2-pyrrolidone and mixing therewith, coating the mixture onto a copper foil current collector, drying and pressure molding to fabricate a negative electrode sheet by stamping out to a diameter of 16 mmφ, adding 2,4-di-tert-butylphenyl methanesulfonate at 2% by weight relative to the nonaqueous electrolytic solution instead of the 2,4-di-tert-butylphenyl trifluoromethanesulfonate used in Example 1, using the resulting a coin shaped battery to charge for 5 hours to a cutoff voltage of 3.8 V at a constant current of 2 mA and constant voltage at room temperature (25° C.) and then discharging to a cutoff voltage of 2.0 V at a constant current of 2 mA, and repeating this charging and discharging for 100 cycles. The results are shown in Table 4.

Comparative Example 5

A coin shaped battery was fabricated and measured for battery properties by preparing a nonaqueous electrolytic solution in the same manner as Example 15 with the exception of not adding the 2,4-di-tert-butylphenyl methanesulfonate used in Example 15. The results are shown in Table 4.

comparison with Comparative Example 1. In addition, in the case of adding 2,4-di-methylphenyl trifluoromethanesulfonate having two methyl groups instead of two tert-butyl groups of 2,4-di-tert-butylphenyl trifluoromethanesulfonate compound of Example 1, cycle maintenance rate decreased as compared with Comparative Example 1. In this manner, unexpected unique effects were determined to be brought about as a result of having two tert-butyl groups on the benzene ring of a phenyl alkylsulfonate or phenyl arylsulfonate.

In addition, similar effects are also observed in the case of using a lithium-containing olivine-type phosphate for the positive electrode (Example 15) or using Si (Example 14) or Sn for the negative electrode.

Example 16

Preparation of Electrolytic Solution

LiPF$_6$ to a concentration of 0.95 M and LiN(SO$_2$CF$_3$)$_2$ to a concentration of 0.05 M were dissolved in a nonaqueous solvent mixture including or consisting of ethylene carbonate (EC), vinylene carbonate (VC), methyl ethyl carbonate (MEC) and diethyl carbonate (DEC) prepared at a ratio of 28:2:35:35 (volumetric ratio) followed by the addition of an added compound in the form of 2-tert-butylphenyl trifluoromethanesulfonate at 0.1% by weight relative to a nonaqueous electrolytic solution to prepare a nonaqueous electrolytic solution.

Fabrication of Lithium Ion Secondary Battery

LiCoO$_2$ (positive electrode active material) at a ratio of 92% by weight, acetylene black (conducting agent) at a ratio of 3% by weight and polyvinylidene fluoride (binder) at a ratio of 5% by weight were mixed followed by the addition of a solvent in the form of 1-methyl-2-pyrrolidone solvent and mixing therewith and then coating the mixture onto an aluminum foil current collector, drying and pressure molding to prepare a positive electrode sheet in the form of a strip by cutting to a prescribed size. Artificial graphite (negative electrode active material) at a ratio of 95% by weight and polyvinylidene fluoride (binder) at a ratio of 5% by weight were

TABLE 4

| | Added Compound | Amount Added (wt %) | Capacity Retention After 100 Cycle (%) |
|---|---|---|---|
| Example 15 | 2,4-di-tert-butylphenyl methanesulfonate | 2 | 96 |
| Comp. Ex. 5 | None | — | 82 |

The lithium secondary batteries of Examples 1 to 13 described above demonstrate battery performance having superior cycle performance in comparison with the lithium secondary battery of Comparative Example 1 not containing a di-tert-butylphenyl alkylsulfonate compound or di-tert-butylphenyl arylsulfonate compound. In addition, in the case of adding phenyl trifluoromethanesulfonate not having two tert-butyl groups instead of the 2,4-di-tert-butylphenyl trifluoromethanesulfonate compound of Example 1 as in Comparative Example 2, effects of addition are not observed at all in then mixed followed by the addition of 1-methyl-2-pyrrolidone solvent and mixing therewith and then coating the mixture onto a copper foil current collector, drying and pressure molding to prepare a negative electrode sheet in the form of a strip by cutting to a prescribed size. The positive electrode sheet, a microporous polyethylene film separator, the negative electrode sheet and the separator were laminated in that order followed by wrapping into the shape of a spiral. This spiraled material was then housed in a nickel-plated, cylindrical cell can made of iron serving as a negative electrode terminal. Moreover, injecting an electrolytic solution, a battery cover having a positive electrode terminal was then fastened to the cell can through a gasket to fabricate a cylindrical battery. Furthermore, the positive electrode terminal used a positive electrode sheet and an aluminum lead tab, and the negative electrode can used a negative electrode sheet and a nickel lead tab, and were internally connected within the battery in advance.

Measurement of Cycle Performance

The battery fabricated in the manner described above was charged for 3 hours to a cutoff voltage of 4.2 V at a constant current of 1 C and constant voltage in a temperature chamber at 25° C. and then discharged to a discharge voltage of 2.7 V at a constant current of 1 C, and repeating this charging and discharging for 100 cycles. The capacity maintenance rate (%) after cycling was determined according to the following formula. The capacity maintenance rate was 78% where the capacity maintenance rate (%)=(discharge capacity after 100 cycles/discharge capacity of 1st cycle)×100.

Evaluation of Storage Properties

A different cylindrical battery using an electrolytic solution having the same composition as described above was charged for 7 hours to a cutoff voltage of 4.2 V at a constant current of 0.2 C and constant voltage in a constant temperature chamber at 25° C., placed in a constant temperature at 60° C. and then charged for 3 days at a constant voltage of 4.2 V followed by measuring the amount of gas generated using the Archimedean method. The amount of gas generated was 81% based on a value of 100% for the amount of gas generated in Comparative Example 6.

The battery fabrication conditions and battery properties are shown in Table 5.

Examples 17 to 20

Cylindrical batteries were fabricated and measured for battery properties by preparing nonaqueous electrolytic solutions in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2-tert-butylphenyl methanesulfonate at 0.1% by weight, 1% by weight, 5% by weight and 10% by weight, respectively, relative to the nonaqueous electrolytic solution instead of the 2-tert-butylphenyl trifluoromethanesulfonate used in Example 16. The results are shown in Table 5.

Example 21

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2-tert-butylphenyl ethanesulfonate at 1% by weight relative to the nonaqueous electrolytic solution instead of the 2-tert-butylphenyl trifluoromethanesulfonate used in Example 16. The results are shown in Table 5.

Example 22

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2-tert-butylphenyl benzenesulfonate at 1% by weight relative to the nonaqueous electrolytic solution instead of the 2-tert-butylphenyl trifluoromethanesulfonate used in Example 16. The results are shown in Table 5.

Example 23

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2-tert-butylphenyl p-toluenesulfonate at 1% by weight relative to the nonaqueous electrolytic solution instead of the 2-tert-butylphenyl trifluoromethanesulfonate used in Example 16. The results are shown in Table 5.

Example 24

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 3-tert-butylphenyl methanesulfonate at 1% by weight relative to the nonaqueous electrolytic solution instead of the 2-tert-butylphenyl trifluoromethanesulfonate used in Example 16. The results are shown in Table 5.

Example 25

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 3-tert-butylphenyl ethanesulfonate at 1% by weight relative to the nonaqueous electrolytic solution instead of the 2-tert-butylphenyl trifluoromethanesulfonate used in Example 16. The results are shown in Table 5.

Example 26

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 4-tert-butylphenyl methanesulfonate at 1% by weight relative to the nonaqueous electrolytic solution carbonate (DEC) prepared to a ratio of 28:2:35:35 (volumetric ratio), and adding 2-methylphenyl trifluoromethanesulfonate at 0.1% by weight relative to the nonaqueous electrolytic solution instead of the 2-tert-butylphenyl trifluoromethanesulfonate used in Example 16. The results are shown in Table 5.

TABLE 5

| | Added Compound | Added Amount (wt %) | Capacity Retention After 100 Cycle (%) | Amount of Gas Generated (%) |
|---|---|---|---|---|
| Example 16 | 2-tert-butylphenyl trifluoromethanesulfonate | 0.1 | 78 | 81 |
| Example 17 | 2-tert-butylphenyl methanesulfonate | 0.1 | 80 | 77 |
| Example 18 | 2-tert-butylphenyl methanesulfonate | 1 | 87 | 72 |
| Example 19 | 2-tert-butylphenyl methanesulfonate | 5 | 86 | 74 |
| Example 20 | 2-tert-butylphenyl methanesulfonate | 10 | 82 | 79 |
| Example 21 | 2-tert-butylphenyl ethanesulfonate | 1 | 85 | 73 |
| Example 22 | 2-tert-butylphenyl benzenesulfonate | 1 | 82 | 75 |
| Example 23 | 2-tert-butylphenyl p-toluenesulfonate | 1 | 80 | 76 |
| Example 24 | 3-tert-butylphenyl methanesulfonate | 1 | 83 | 76 |
| Example 25 | 3-tert-butylphenyl ethanesulfonate | 1 | 81 | 77 |
| Example 26 | 4-tert-butylphenyl methanesulfonate | 1 | 85 | 74 |
| Comp. Ex. 6 | None | — | 71 | 100 |
| Comp. Ex. 7 | Phenyl trifluoromethanesulfonate | 0.1 | 73 | 91 |
| Comp. Ex. 8 | 2-methylphenyl trifluoromethanesulfonate | 0.1 | 69 | 93 | instead of the 2-tert-butylphenyl trifluoromethanesulfonate used in Example 16. The results are shown in Table 5.

Comparative Example 6

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), but not adding the 2-tert-butylphenyl trifluoromethanesulfonate used in Example 16. The results are shown in Table 5.

Comparative Example 7

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding phenyl trifluoromethanesulfonate at 0.1% by weight relative to the nonaqueous electrolytic solution instead of the 2-tert-butylphenyl trifluoromethanesulfonate used in Example 16. The results are shown in Table 5.

Comparative Example 8

A cylindrical battery was fabricated and measured for battery properties by preparing a nonaqueous electrolytic solution in the same manner as Example 16 with the exception of dissolving $LiPF_6$ to a concentration of 0.95 M and LiN$(SO_2CF_3)_2$ to 0.05 M in a nonaqueous solvent mixture including or consisting of ethylene carbonate (EC), vinylene carbonate (VC), methyl ethyl carbonate (MEC) and diethyl Example 27

A cylindrical battery was fabricated and measured for battery properties by preparing a nonaqueous electrolytic solution in the same manner as Example 16 with the exception of using Si for the negative electrode active substance instead of artificial graphite, mixing Si (negative electrode active substance) at a ratio of 75% by weight, artificial graphite (conducting agent) at a ratio of 10% by weight, acetylene black (conducting agent) at a ratio of 10% by weight and polyvinylidene fluoride (binder) at a ratio of 5% by weight, adding 1-methyl-2-pyrrolidone solvent and mixing therewith, coating the mixture onto a copper foil current collector, drying and pressure molding to fabricate a positive electrode sheet in the form of a strip by cutting to a prescribed size, dissolving $LiPF_6$ to a concentration of 0.95 M and $LiBF_4$ to a concentration of 0.05 M in a nonaqueous solvent mixture including or consisting of ethylene carbonate (EC), vinylene carbonate (VC), methyl ethyl carbonate (MEC) and diethyl carbonate (DEC) prepared to a ratio of 28:2:35:35 (volumetric ratio), and adding 2-tert-butylphenyl methanesulfonate at 2% by weight relative to the nonaqueous electrolytic solution instead of adding the 2-tert-butylphenyl trifluoromethanesulfonate used in Example 16. The results are shown in Table 6. Furthermore, the amount of gas generated was determined based on a value of 100% for the amount of gas generated in Comparative Example 9.

Comparative Example 9

A cylindrical battery was fabricated and measured for battery properties by preparing a nonaqueous electrolytic solution in the same manner as Example 27 with the exception of not adding the 2-tert-butylphenyl methanesulfonate used in Example 27. The results are shown in Table 6.

TABLE 6

| | Added Compound | Added Amount (wt %) | Capacity Retention After 100 Cycle (%) | Amount of Gas Generated (%) |
|---|---|---|---|---|
| Example 27 | 2-tert-butylphenyl methanesulfonate | 2 | 78 | 76 |
| Comp. Ex. 9 | None | — | 42 | 100 |

Example 28

A cylindrical battery was fabricated and measured for battery properties by preparing a nonaqueous electrolytic solution in the same manner as Example 16 with the exception of using LiFePO$_4$ for the positive electrode active substance instead of LiCoO$_2$, mixing LiFePO$_4$ (positive electrode active substance) at a ratio of 90% by weight, acetylene black (conducting agent) at a ratio of 5% by weight and polyvinylidene fluoride (binder) at a ratio of 5% by weight, adding 1-methyl-2-pyrrolidone solvent and mixing therewith, coating the mixture onto an aluminum foil current collector, drying and pressure molding to fabricate a positive electrode sheet in the form of a strip by cutting to a prescribed size, mixing graphite coated with lowly crystalline carbon (negative electrode active substance) at a ratio of 95% by weight and polyvinylidene fluoride (binder) at a ratio of 5% by weight, adding 1-methyl-2-pyrrolidone solvent and mixing therewith, coating the mixture onto a copper foil current collector, drying and pressure molding to fabricate a negative electrode sheet, adding 2-tert-butylphenyl methanesulfonate at 2% by weight relative to the nonaqueous electrolytic solution instead of the 2-tert-butylphenyl trifluoromethanesulfonate used in Example 16, using the resulting cylindrical battery to charge to a cutoff voltage of 3.8 V instead of 4.2 V and discharge to a cutoff voltage of 2.0 V instead of 2.7 V. The results are shown in Table 7. Furthermore, the amount of gas generated was determined based on a value of 100% for the amount of gas generated in Comparative Example 10.

Comparative Example 10

A cylindrical battery was fabricated and measured for battery properties by preparing a nonaqueous electrolytic solution in the same manner as Example 28 with the exception of not adding the 2-tert-butylphenyl methanesulfonate used in Example 28. The results are shown in Table 7.

TABLE 7

| | Added Compound | Added Amount (wt %) | Capacity Retention After 100 Cycle (%) | Amount of Gas Generated (%) |
|---|---|---|---|---|
| Example 28 | 2-tert-butylphenyl methanesulfonate | 2 | 93 | 78 |
| Comp. Ex. 10 | None | — | 78 | 100 |

The lithium secondary batteries of Examples 16 to 26 described above demonstrate superior cycle performance and have the effect of inhibiting generation of gas in comparison with the lithium secondary battery of Comparative Example 6 not containing a tert-butylphenyl alkylsulfonate compound or tert-butylphenyl arylsulfonate compound. In addition, in the case of adding phenyl trifluoromethanesulfonate not having a tert-butyl group instead of the 2-tert-butylphenyl trifluoromethanesulfonate compound of Example 16 as in Comparative Example 7, effects of addition are not observed at all in comparison with Comparative Example 6. In addition, in the case of adding 2-methylphenyl trifluoromethanesulfonate having a methyl group instead of the tert-butyl group of the 2-tert-butylphenyl trifluoromethanesulfonate compound of Example 16, capacity retention decreased and the effect of inhibiting generation of gas was small as compared with Comparative Example 6. In this manner, unexpected unique effects were determined to be brought about as a result of having a tert-butyl group on the benzene ring of a phenyl alkylsulfonate or phenyl arylsulfonate.

In addition, similar effects are also observed in the case of using a lithium-containing olivine-type phosphate for the positive electrode (Example 28) or using Si (Example 27) or Sn for the negative electrode.

Although the disclosed embodiments have been described and illustrated with a certain degree of particularity, it is understood that the disclosure has been made only by way of example, and that numerous changes in the conditions and order of steps can be resorted to by those skilled in the art without departing from the spirit and scope of the disclosed embodiments.

The invention claimed is:

1. A tert-butylphenyl alkylsulfonate compound or tert-butylphenyl arylsulfonate compound represented by general formula (I):

[C1]

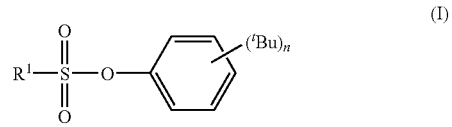

(wherein, R$^1$ represents (i) a fluoro-substituted alkyl group, (ii) a non-substituted alkyl group or (iii) a substituted or non-substituted phenyl group, and n represents an integer of 1 to 2, provided that in the case n=1, the substitution position of the $^t$Bu group is the 2 position or 3 position, in the case the substitution position of the $^t$Bu group is the 2 position, R$^1$ represents a non-substituted alkyl group having 2 to 4 carbon atoms, in the case the substitution position of the $^t$Bu group is the 3 position, R$^1$ represents a non-substituted alkyl group having 1 to 4 carbon atoms, and in the case n=2, the substitution positions of the $^t$Bu group are any of the 2,4 position, 2,5 position, 2,6 position or 3,5 position, and in the case $^t$Bu groups are present at the 3,5 position, R$^1$ represents a non-substituted alkyl group having 1 to 4 carbon atoms or a non-substituted phenyl group).

2. The tert-butylphenyl alkylsulfonate compound or the tert-butylphenyl arylsulfonate compound according to claim 1, wherein the compound represented by the general formula (I) is one type of compound selected from 2,4-di-tert-butylphenyl methanesulfonate, 2,6-di-tert-butylphenyl methanesulfonate, 3,5-di-tert-butylphenyl methanesulfonate, 2,5-di-tert-butylphenyl methanesulfonate, 2,4-di-tert-butylphenyl ethanesulfonate, 2,6-di-tert-butylphenyl ethanesulfonate, 3,5-di-tert-butylphenyl ethanesulfonate and 2,4-di-tert-butylphenyl trifluoromethanesulfonate.

3. The tert-butylphenyl alkylsulfonate compound or the tert-butylphenyl arylsulfonate compound according to claim 1, wherein the compound represented by the general formula (I) is 2,4-di-tert-butylphenyl benzenesulfonate or 2,4-di-tert-butylphenyl p-toluenesulfonate.

4. The tert-butylphenyl alkylsulfonate compound or the tert-butylphenyl arylsulfonate compound according to claim 1, wherein the compound represented by the general formula (I) is one type of tert-butylphenyl alkylsulfonate compound selected from 3-tert-butylphenyl methanesulfonate, 2-tert-butylphenyl ethanesulfonate and 3-tert-butylphenyl ethanesulfonate.

5. A nonaqueous electrolytic solution for a lithium secondary battery comprising an electrolyte salt dissolved in a nonaqueous solvent comprising the compound of claim 1.

6. The nonaqueous electrolytic solution for a lithium secondary battery of claim 5, wherein the nonaqueous solvent comprises 0.01 to 10% by weight of the compound of claim 1.

7. The nonaqueous electrolytic solution for a lithium secondary battery according to claim 5, wherein the electrolyte salt is at least one type selected from $LiPF_6$, $LiBF_4$, $LiN(SO_2CF_3)_2$, and $LiN(SO_2C_2F_5)_2$.

8. The nonaqueous electrolytic solution for a lithium secondary battery according to claim 5, wherein the electrolyte salt comprises $LiPF_6$ and additionally comprises at least one type selected from $LiBF_4$, $LiN(SO_2CF_3)_2$, and $LiN(SO_2C_2F_5)_2$.

9. The nonaqueous electrolytic solution for a lithium secondary battery according to claim 5, wherein the nonaqueous solvent contains a cyclic carbonate and a chain carbonate.

10. The nonaqueous electrolytic solution for a lithium secondary battery according to claim 9, wherein the cyclic carbonate is at least one type selected from ethylene carbonate, propylene carbonate, butylene carbonate, fluoroethylene carbonate, vinylene carbonate, and vinylethylene carbonate and wherein the chain carbonate contains an asymmetric carbonate selected from methyl ethyl carbonate, methyl propyl carbonate, methyl isopropyl carbonate, methyl butyl carbonate, and ethyl propyl carbonate.

11. The nonaqueous electrolytic solution for a lithium secondary battery according to claim 9, wherein the ratio between the cyclic carbonate and chain carbonate is 10:90 to 40:60 as the volume ratio.

12. A lithium secondary battery comprising a positive electrode, a negative electrode and the nonaqueous electrolytic solution of claim 5.

13. A tert-butylphenyl alkylsulfonate compound or tert-butylphenyl arylsulfonate compound represented by general formula (I):
[C1]

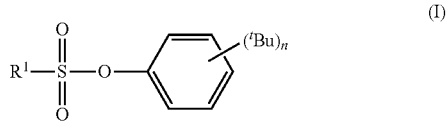

wherein, $R^1$ represents a substituted or non-substituted alkyl group or substituted or non-substituted phenyl group, and n represents an integer of 1 to 2, provided that in the case n=1, the substitution position of the $^tBu$ group is the 2 position or 3 position, in the case the substitution position of the $^tBu$ group is the 2 position, $R^1$ represents a non-substituted alkyl group having 2 to 4 carbon atoms, in the case the substitution position of the $^tBu$ group is the 3 position, $R^1$ represents a non-substituted alkyl group having 1 to 4 carbon atoms, and in the case n=2, the substitution positions of the $^tBu$ group are any of the 2,4 position, 2,5 position, 2,6 position or 3,5 position, and in the case $^tBu$ groups are present at the 2,4 position or 3,5 position, $R^1$ represents a non-substituted alkyl group having 1 to 4 carbon atoms or a non-substituted phenyl group.

14. A nonaqueous electrolytic solution for a lithium secondary battery comprising an electrolyte salt dissolved in a nonaqueous solvent comprising the compound of claim 13.

15. The nonaqueous electrolytic solution for a lithium secondary battery of claim 14, wherein the nonaqueous solvent comprises 0.01 to 10% by weight of the compound of claim 13.

16. The nonaqueous electrolytic solution for a lithium secondary battery according to claim 14, wherein the electrolyte salt is at least one type selected from $LiPF_6$, $LiBF_4$, $LiN(SO_2CF_3)_2$, and $LiN(SO_2C_2F_5)_2$.

17. The nonaqueous electrolytic solution for a lithium secondary battery according to claim 14, wherein the electrolyte salt comprises $LiPF_6$ and additionally comprises at least one type selected from $LiBF_4$, $LiN(SO_2CF_3)_2$, and $LiN(SO_2C_2F_5)_2$.

18. The nonaqueous electrolytic solution for a lithium secondary battery according to claim 14, wherein the nonaqueous solvent contains a cyclic carbonate and a chain carbonate.

19. The nonaqueous electrolytic solution for a lithium secondary battery according to claim 18, wherein the cyclic carbonate is at least one type selected from ethylene carbonate, propylene carbonate, butylene carbonate, fluoroethylene carbonate, vinylene carbonate, and vinylethylene carbonate and wherein the chain carbonate contains an asymmetric carbonate selected from methyl ethyl carbonate, methyl propyl carbonate, methyl isopropyl carbonate, methyl butyl carbonate, and ethyl propyl carbonate.

20. The nonaqueous electrolytic solution for a lithium secondary battery according to claim 18, wherein the ratio between the cyclic carbonate and chain carbonate is 10:90 to 40:60 as the volume ratio.

21. A lithium secondary battery comprising a positive electrode, a negative electrode and the nonaqueous electrolytic solution of claim 15.

22. 2,4-di-tert-butylphenyl trifluoromethanesulfonate.

* * * * *

UNITED STATES PATENT AND TRADEMARK OFFICE
CERTIFICATE OF CORRECTION

PATENT NO. : 8,546,599 B2  
APPLICATION NO. : 12/530206  
DATED : October 1, 2013  
INVENTOR(S) : Koji Abe Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this

Fifteenth Day of September, 2015

Michelle K. Lee
*Director of the United States Patent and Trademark Office*